(12) United States Patent
Dutta et al.

(10) Patent No.: US 11,986,564 B2
(45) Date of Patent: May 21, 2024

(54) SELF-ADJUSTING DAMPER BASED LINEAR ALIGNMENT SYSTEM

(71) Applicant: AMERICAN STERILIZER COMPANY, Mentor, OH (US)

(72) Inventors: Sandeepan Dutta, Lyndhurst, OH (US); Michael Rabinovich, Solon, OH (US); Kenneth J. Klobusnik, Lake City, PA (US)

(73) Assignee: American Sterilizer Company, Mentor, OH (US)

( * ) Notice: Subject to any disclaimer, the term of this patent is extended or adjusted under 35 U.S.C. 154(b) by 107 days.

(21) Appl. No.: 17/737,293

(22) Filed: May 5, 2022

(65) Prior Publication Data

US 2022/0257808 A1    Aug. 18, 2022

Related U.S. Application Data

(62) Division of application No. 15/634,133, filed on Jun. 27, 2017, now Pat. No. 11,351,277.

(51) Int. Cl.
*E05D 15/06* (2006.01)
*A61L 2/07* (2006.01)
(Continued)

(52) U.S. Cl.
CPC .............. *A61L 2/07* (2013.01); *E05D 15/165* (2013.01); *E06B 3/4423* (2013.01); *E06B 3/443* (2013.01); *E06B 7/20* (2013.01); *A61L 2202/121* (2013.01); *E05Y 2201/434* (2013.01); *E05Y 2201/454* (2013.01); *E05Y 2201/606* (2013.01); *E05Y 2201/654* (2013.01); *E05Y 2201/688* (2013.01);
(Continued)

(58) Field of Classification Search
CPC ... A61L 2/07; A61L 2202/121; E05D 15/165; E05D 15/20; E05D 15/22; E05D 2015/225; E06B 3/4423; E06B 3/443; E06B 3/44; E06B 3/4407; E06B 7/20; E06B 7/205; E06B 7/21; E06B 7/215; E06B 7/22; E06B 7/2307; E05Y 2201/434; E05Y 2201/454; E05Y 2201/606; E05Y 2201/654; E05Y 2201/688; E05Y 2600/41; E05Y 2900/20
See application file for complete search history.

(56) References Cited

U.S. PATENT DOCUMENTS 1,554,494 A * 9/1925 Fleckenstein ........... E05D 13/06
                                                    49/417
1,985,976 A * 1/1935 Clark ...................... E05D 15/24
                                                    16/104
(Continued)

FOREIGN PATENT DOCUMENTS

WO    WO-2012009022 A2 * 1/2012 ........... E05D 15/242

*Primary Examiner* — Chuck Y Mah
(74) *Attorney, Agent, or Firm* — KUSNER & JAFFE

(57) ABSTRACT

A steam sterilizer having a door movable relative to an opening between a first open position and a second closed position. A plurality of spaced-apart roller assemblies are aligned along edges of the door to align the door relative to the opening as the door moves between the open and closed position. Each of the roller assemblies are comprised of a cylindrical roller having an outer annual recess extending along the periphery thereof. The recess is dimensioned to receive a lateral edge of the door. The roller is mounted on a shaft and is movable against a biasing force axially along the axis of the shaft.

10 Claims, 7 Drawing Sheets

(51) Int. Cl.
  *E05D 15/16* (2006.01)
  *E06B 3/44* (2006.01)
  *E06B 7/20* (2006.01)

(52) U.S. Cl.
  CPC ....... *E05Y 2600/41* (2013.01); *E05Y 2900/20* (2013.01); *E06B 3/4407* (2013.01)

(56) References Cited

U.S. PATENT DOCUMENTS

| | | | |
|---|---|---|---|
| 2,541,179 A | 2/1951 | Sponsler | |
| 2,755,081 A | 7/1956 | Johnson | |
| 2,807,836 A | 10/1957 | Knowles | |
| 3,144,956 A | 8/1964 | Anderson | |
| 3,144,957 A | 8/1964 | Anderson | |
| 3,386,203 A | 6/1968 | Butler | |
| 3,413,987 A | 12/1968 | Brown | |
| 3,959,849 A | 6/1976 | Marquardt | |
| 4,048,687 A | 9/1977 | Kato | |
| 4,403,448 A * | 9/1983 | Lesher | E05D 15/1005 49/225 |
| 4,565,031 A | 1/1986 | Sakamoto | |
| 4,708,410 A | 11/1987 | Mazaki | |
| 4,872,585 A | 10/1989 | Kim | |
| 4,880,046 A * | 11/1989 | Gesy | E05F 15/668 160/40 |
| 4,901,474 A | 2/1990 | Bayard | |
| 5,148,631 A | 9/1992 | Bayard | |
| 5,237,777 A | 8/1993 | Houston | |
| 5,249,392 A | 10/1993 | Houston | |
| 5,397,138 A | 3/1995 | Mangelsdorf | |
| 5,535,805 A * | 7/1996 | Kellogg | E06B 9/581 160/281 |
| 5,543,119 A | 8/1996 | Sutter | |
| 5,547,453 A | 8/1996 | Di Perna | |
| 5,571,488 A | 11/1996 | Beerstecher | |
| 5,723,090 A | 3/1998 | Beerstecher | |
| 5,845,363 A | 12/1998 | Brempell | |
| 5,863,498 A | 1/1999 | Houston | |
| 6,017,105 A | 1/2000 | Goughnour | |
| 6,264,901 B1 | 7/2001 | Anderson | |
| 6,416,144 B1 | 7/2002 | Houston | |
| 6,443,148 B1 * | 9/2002 | Rodocker | A61G 10/026 128/205.26 |
| 6,779,567 B1 | 8/2004 | Szatmary | |
| 6,871,448 B1 | 3/2005 | Kline | |
| 6,928,696 B2 * | 8/2005 | Wartman | E05D 15/24 16/99 |
| 7,121,042 B2 * | 10/2006 | Robert | E05D 15/20 49/260 |
| 7,124,538 B1 | 10/2006 | Kline | |
| 7,361,303 B2 | 4/2008 | Kantor | |
| 8,152,027 B1 | 4/2012 | Baker | |
| 8,261,941 B2 | 9/2012 | Woo | |
| 8,684,065 B2 * | 4/2014 | Peterson | E05D 15/165 160/209 |
| 8,745,925 B2 | 6/2014 | Halfon | |
| 9,187,941 B2 | 11/2015 | Therrien | |
| 9,242,374 B2 | 1/2016 | Oaki | |
| 9,708,844 B2 | 7/2017 | Glogowski | |
| 2005/0132533 A1 | 6/2005 | Nguyen | |
| 2008/0017649 A1 | 1/2008 | Elgan | |
| 2010/0043172 A1 | 2/2010 | Nezu | |
| 2011/0088327 A1 * | 4/2011 | Meichtry | E05D 15/165 16/96 R |
| 2014/0163526 A1 | 6/2014 | Cabiri | |
| 2015/0075077 A1 * | 3/2015 | Aragon | E06B 1/522 49/420 |

* cited by examiner

SELF-ADJUSTING DAMPER BASED LINEAR ALIGNMENT SYSTEM

CROSS-REFERENCE TO RELATED APPLICATIONS

This is a Divisional of U.S. application Ser. No. 15/634,133, filed Jun. 27, 2017, and is hereby fully incorporated herein by reference.

FIELD OF THE INVENTION

The present invention relates generally to sterilizers, and more particularly, to a system for aligning doors on a steam sterilize.

BACKGROUND OF THE INVENTION

Steam sterilizers are well known and widely used in hospitals, laboratories and other facilities for sterilizing and decontaminating many types of articles. Steam sterilizers define sterilization chambers that often operate under pressure or vacuum during a sterilization cycle. Access to the sterilization chamber is through an access opening at one end of the sterilizer. On some conventional steam sterilizers, access to the sterilization chamber is controlled by a door assembly that moves vertically relative to the access opening to the sterilization chamber. A seal typically surrounds the access opening and engages the inner surface of the door to form a seal around the access opening to the sterilization chamber. As indicated above, pressure within the chamber can exceed atmospheric pressure or may be below atmospheric pressure, thereby exerting forces against the inner surface of the door to force the door away from the sterilization chamber or to draw the door assembly toward the sterilization chamber.

Guiding systems are required to guide the door assembly relative to the access opening. Hooks or blocks are typically provided to prevent the door from moving significantly away from the sterilization chamber when the sterilization chamber is under high pressure. Heretofore, the door guiding mechanism was comprised of a linear guide/rail system that employed ball bearings or roller-bearing sliders that aligned the door for movement within a plane that spans the access opening. Such linear guide/rail systems require precision parts, aligned to facilitate movement of the door assembly in a single plane. In other words, guide/rail systems known heretofore do not allow movement of the door toward or away from the access opening to a sterilization chamber. This requires seal arrangements that can project outwards into engagement with the inner surface of the door to seal the sterilization chamber. In addition, such guide systems require precise alignment of the door to ensure proper sealing of the sterilization chamber.

The present invention provides a door alignment system that is simpler in design and cost, and allows limited movement of the door assembly toward and away from the access opening during sealing of the access opening and during operation of the sterilizer.

SUMMARY OF THE INVENTION

In accordance with the present invention, there is provided a steam sterilizer having a sterilization chamber and an opening for accessing the sterilization chamber. A door is movable relative to the opening between an open position and a closed position. A seal surrounds the opening. The seal is movable against the door when the door is in the closed position to seal the door relative to the sterilization chamber.

A plurality of spaced-apart roller assemblies are aligned along edges of the door to align the door relative to the opening as the door moves between an open and closed position. Each of the roller assemblies is comprised of a cylindrical roller having an outer annual recess extending along the periphery thereof. The recess is dimensioned to receive a lateral edge of the door. The roller is mounted on a shaft and is movable against a biasing force axially along the axis of the shaft, wherein the plurality of roller assemblies align the door and allow the door to move along a path in a plane and further allow limited movement of the door in a direction perpendicular to the plane.

An advantage of the present invention is a door alignment system for use on a steam sterilizer that allows the door to move across the access opening to the sterilizing chamber to open and close the same, the door alignment system allowing limited movement of the door, when in a closed position, toward and away from the access opening.

Another advantage of the present invention is a door alignment system as described above, that is simpler in design and allows the door assembly to adjust itself relative to the access opening when moving between an open position and a closed position.

Another advantage of the present invention is an alignment assembly as described above, wherein rollers engaging the lateral edges of the door assembly to guide the door between an open and closed position.

Another advantage of the present invention is an alignment system as described above, wherein the rollers allow movement of the door assembly in a direction perpendicular to the plane of the door assembly.

A still further advantage of the present invention is an alignment system as described above, wherein the rollers are mounted to a shaft and are biased axially along the shaft, wherein said rollers are movable along the shaft against the biasing forces.

Another advantage of the present invention is an alignment system as described above, wherein the rollers are movable with the door assembly relative to the access opening.

BRIEF DESCRIPTIONS OF THE DRAWINGS

Referring now to the drawings wherein the showings are for the purpose of illustrating a preferred embodiment of the invention only and not for the purpose of limiting same:

Figure 6:
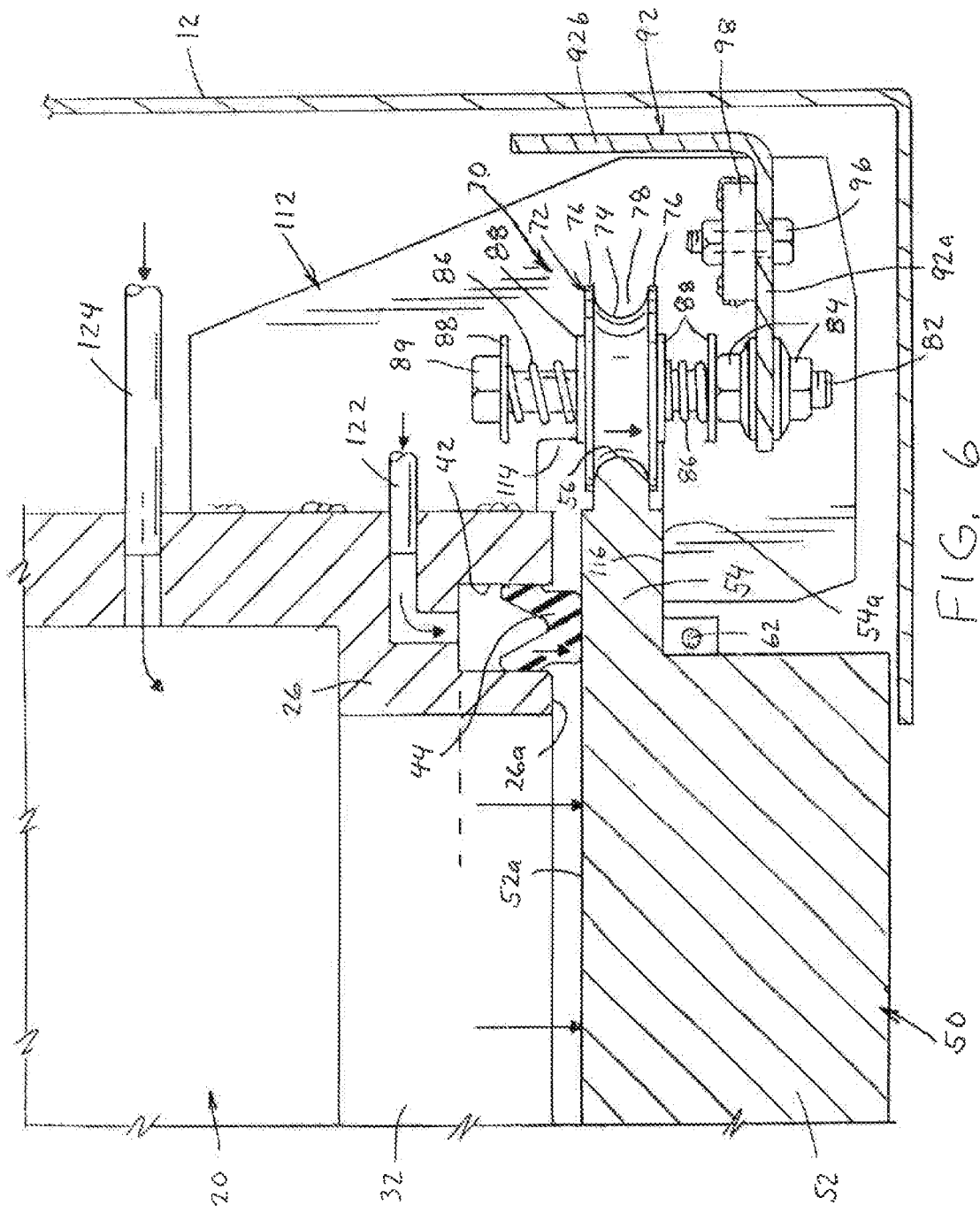
Figure 7:
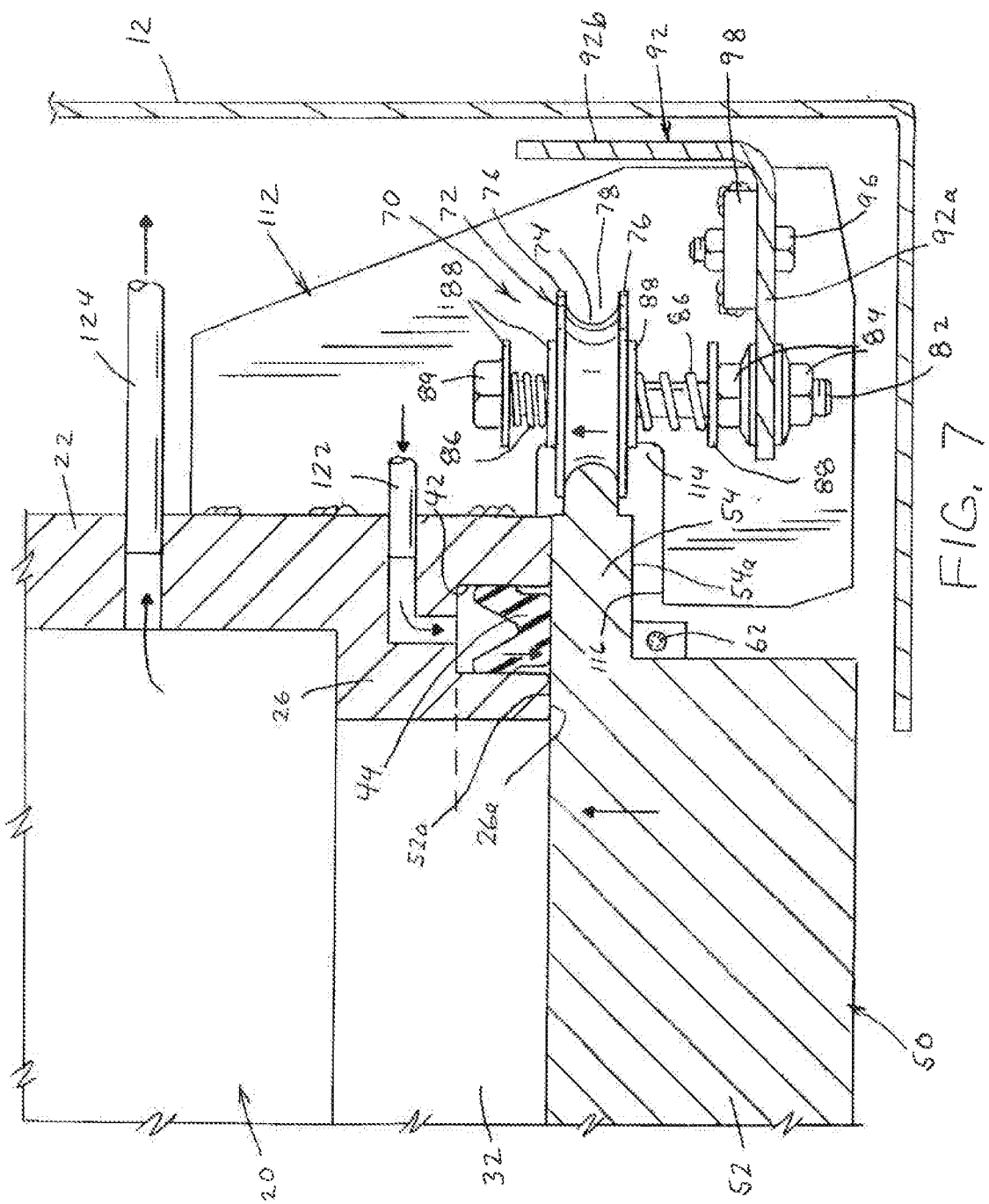

FIG. 6 is a sectional view of the door assembly, roller assembly and clamp assembly, showing the position of the roller assembly and the door assembly when the pressure within the sterilization chamber exceeds the pressure outside of the sterilization chamber is in the second position and the door assembly is forced outwardly away from the sterilization chamber against the inner facing surface of the clamp during conditions; and FIG. 7 is a sectional view of the door assembly, roller assembly and clamp assembly, when the pressure within the sterilizer is below the pressure outside of the sterilization chamber showing the position of the roller assembly when the inner surface of the door assembly is forced against the outer face of the sterilizer.

DETAILED DESCRIPTION OF PREFERRED EMBODIMENTS

Figure 1:
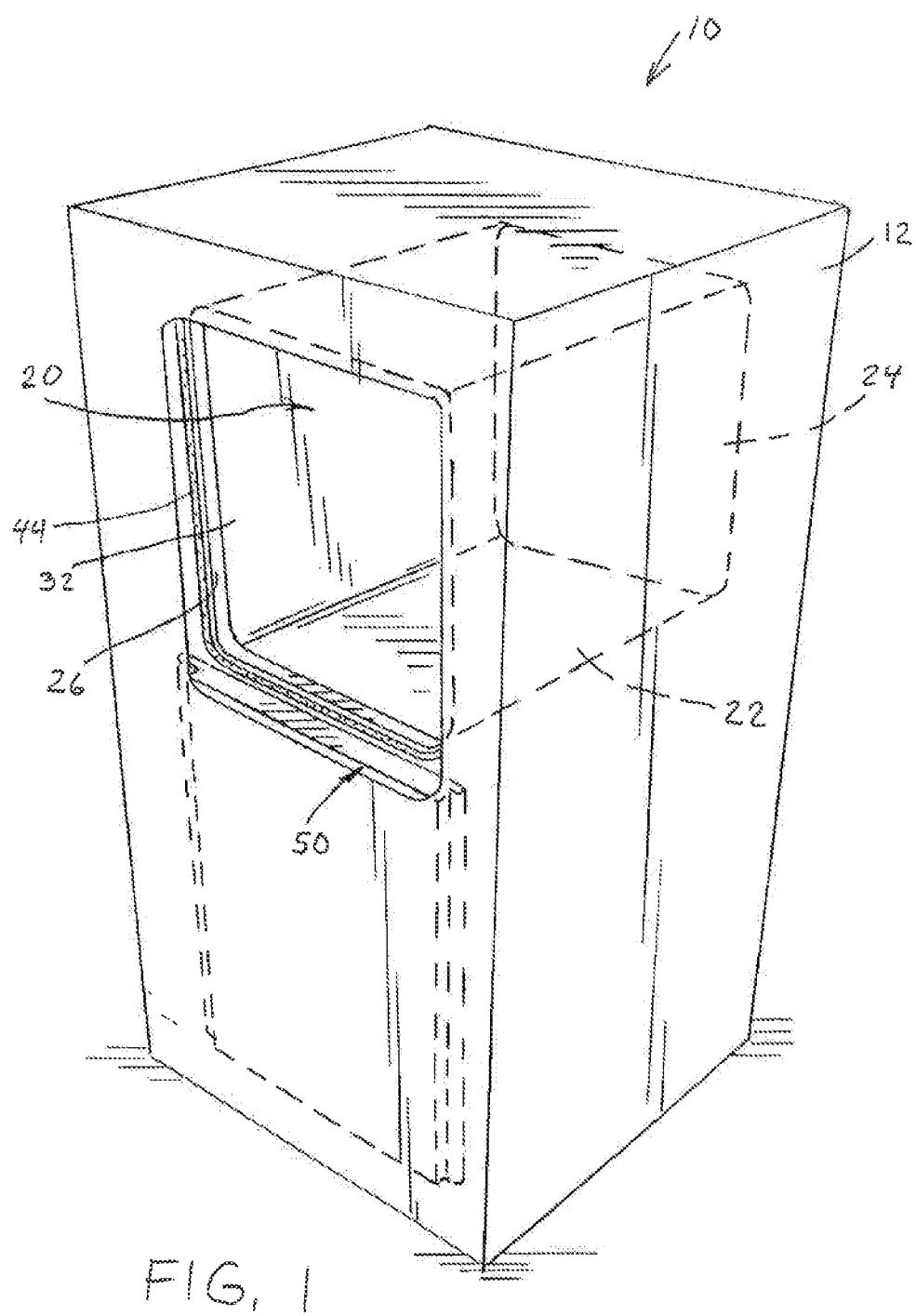
FIG. 1 is a perspective view of a steam sterilizer.

Referring now the drawings wherein the showings are for the purpose of illustrating a preferred embodiment of the invention only, and not for the purpose of limiting same, FIG. 1 shows a perspective view of a conventional steam sterilizer 10. Sterilizer 10 is of a type generally disclosed in U.S. Pat. No. 8,206,660, the disclosure of which is expressly incorporated herein by reference.

Figure 5:
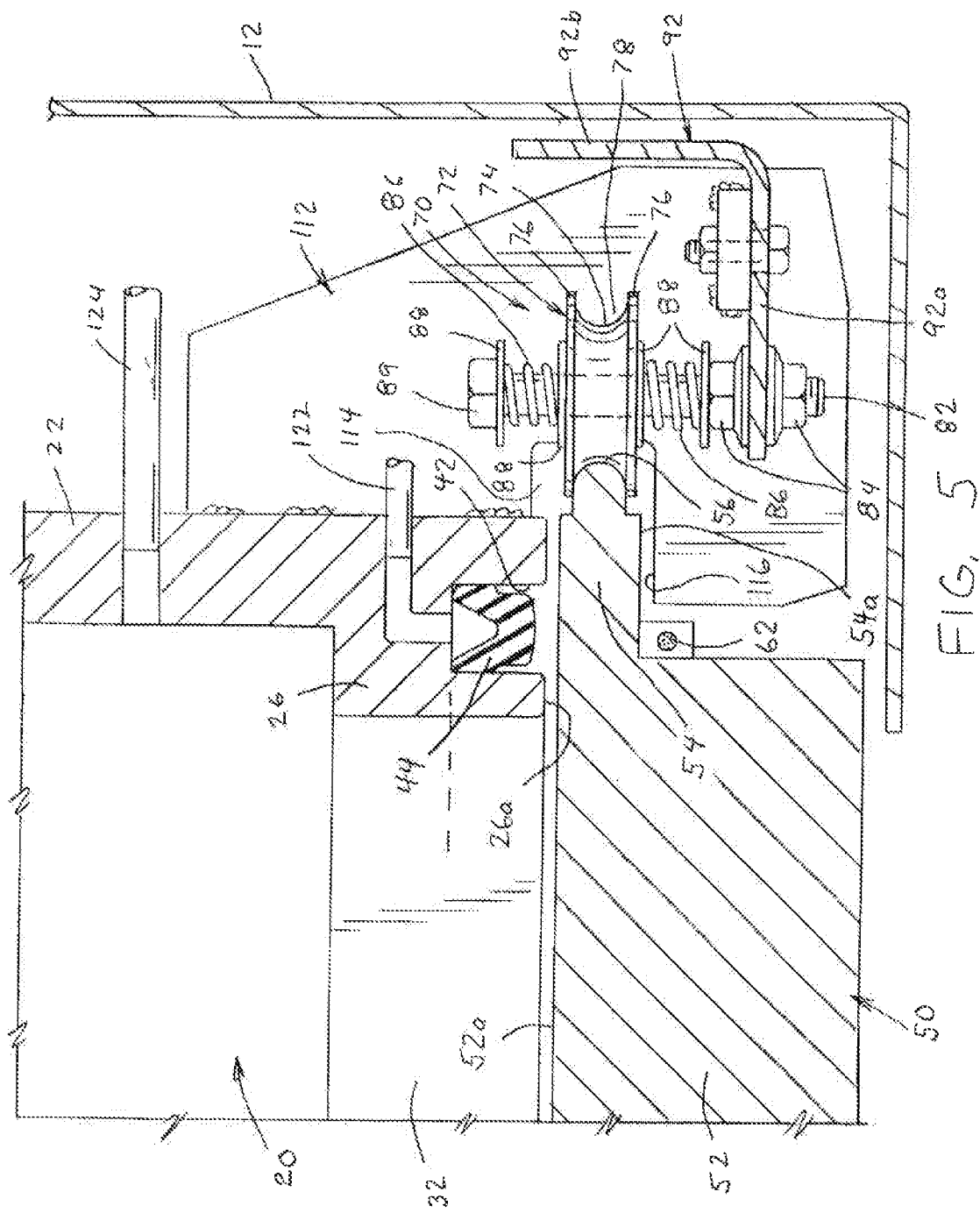
FIG. 5 is a sectional view taken along the lines 5-5 of FIG. 4.

Sterilizer 10 is basically comprised of a housing 12 enclosing an internal sterilization chamber 20. In the embodiment shown, housing 12 is generally rectangular in shape. Sterilizer chamber 20 is generally defined by a rectangular wall 22, a back end wall 24 and a front end wall 26. A rectangular opening 32 is formed in front end wall 26 to define an access opening to sterilization chamber 20 of sterilizer 10. As best seen in FIGS. 5-7, a slot 42 is formed in an outward facing surface 26a of the front end wall 26. Slot 42 extends around the periphery of access opening 32. Slot 42 is dimensioned to receive a seal element 44 that is best described in the aforementioned U.S. Pat. No. 8,206,660.

A movable door assembly 50 is provided to open and close access opening 32 to sterilization chamber 20. Door assembly 50 is basically comprised of a flat plate 52 having an inner surface 52a dimensioned to cover access opening 32 to sterilization chamber 20.

In the embodiment shown, flanges 54 extend from the lateral sides of plate door 52 of assembly 50. Each flange 54 has a contoured, rounded edge surface 56 that extends along the length of the lateral sides of plate door 52 of assembly 50, as best seen in FIGS. 5, 6 and 7.

Figure 2:
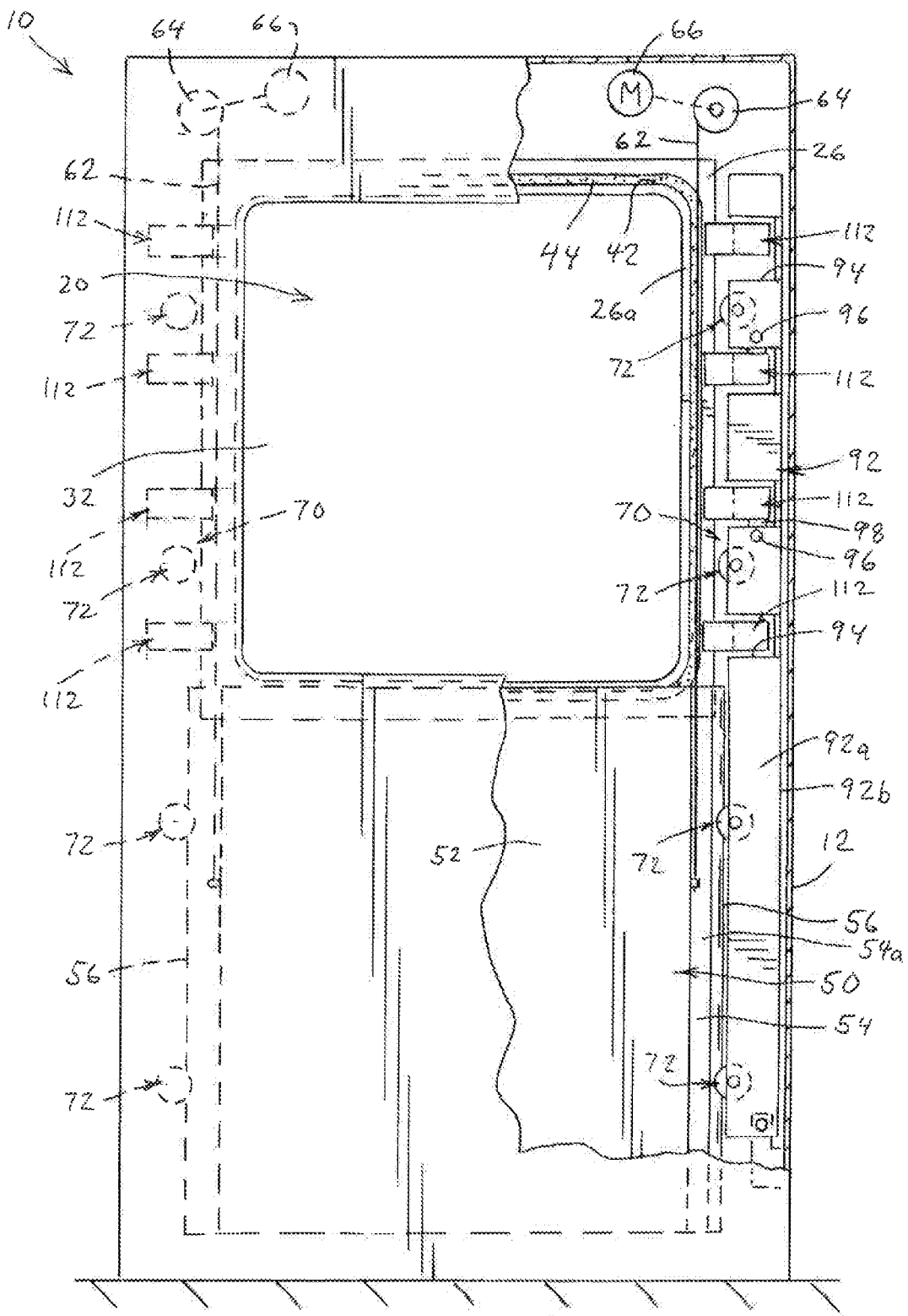
FIG. 2 is a partially-sectioned, front elevational view of the steam sterilizer shown in FIG. 1, showing a door assembly in a first position, allowing access to a sterilization chamber within the steam sterilizer through an access opening.
Figure 3:
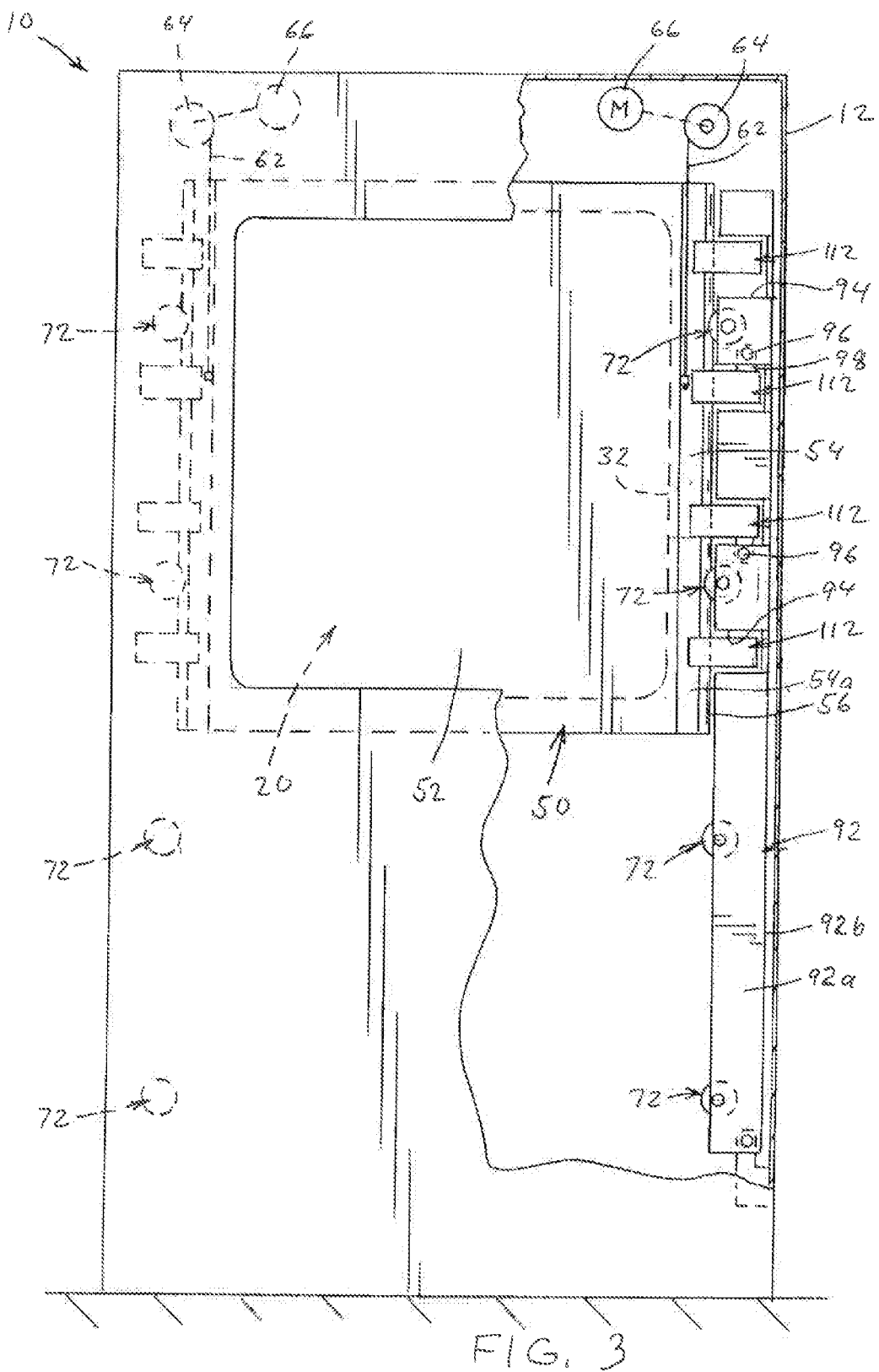
FIG. 3 is a partially-sectioned, front elevational view of the steam sterilizer shown in FIG. 1, showing a door assembly in a second position, closing the access opening to the sterilization chamber.

Door assembly 50 is movable between a first position allowing access to sterilization chamber 20 and a second position closing access to sterilization chamber 20. In the embodiment shown, door assembly 50 is movable between a first, lowered position, as best seen in FIGS. 1 and 2, and a second, elevated and closed position, as best seen in FIG. 3.

Door assembly 50 may be moved by a number of different mechanical drive arrangements. In the embodiment shown, cables 62 attach to an upper portion of door assembly 50 on each side thereof. Each cable 62 is attached to a roller or spool 64 that is driven by a motor 66, as schematically illustrated in FIG. 3. In the embodiment shown, actuation of the motors 66 wind the cables 62 onto or off of spools 64, thereby moving door assembly 50 upward or downward relative to access opening 32 in sterilization chamber 20.

As will be appreciated by those skilled in the art, other types of door transport mechanisms can be employed. For example, hydraulic or pneumatic cylinders may be used to move cables 62 over pulleys. Moreover, linear actuators driven by electric motors may also be used. Cables 62 may be counter-balanced by weights on the opposite ends of cables 62 to facilitate moving the door assembly. In this respect, the method of moving door assembly 50, in and of itself, forms no part of the present invention.

In accordance with one aspect of the present invention, a plurality of aligned roller assemblies 70 are provided along each edge of door assembly 50 to guide door assembly 50 between the first and second positions, i.e., between the open and closed positions. Roller assemblies 70 are best seen in FIGS. 5, 6 and 7. Mounting brackets 92 extend along each side of access opening 32 of sterilizer 10. Mounting brackets 92 are fixedly secured relative to sterilization chamber 20. In the embodiment shown, each mounting bracket 92 is an elongated structure that is generally L-shaped in cross-section to define two leg portions, 92a, 92b. Leg portions 92a, 92b of mounting bracket 92 have spaced apart notches or cutouts 94 formed therein. A mounting bracket 92 is fixedly mounted to each side of access opening 32, as best illustrated in FIG. 3.

Roller assemblies 70 are mounted to mounting brackets 92 to operatively engage edges 56 of the door assemblies 50. Each roller assembly 70 is basically identical, and therefore only one shall be described in detail. Each roller assembly 70 is comprised of a roller 72 mounted to an elongated shaft 82 that in turn is secured to mounting bracket 92.

In the embodiment shown, shaft 82 is mounted to leg portion 92a of mounting bracket 92. In the embodiment shown, serrated, flange nuts 84 secure one end of shaft 82 to leg portion 92a of mounting bracket 92. Shaft 82 is oriented to be generally perpendicular to a plane in which door assembly 50 moves. Roller 72 includes an annular outer surface having a surface profile dimensioned to matingly engage and interact with an outer surface profile of lateral edge 56 of door assembly 50. In the embodiment shown, the surface profile is a concave, semi-cylindrical annular surface 74 that extends about the periphery of roller 72. Concave surface 74 defines annular side walls 76 along the peripheral edges of roller 72. As shown in the drawings, surface 74 defines a recess 78 is dimensioned to receive rounded, lateral edge 56 of door assembly 50 in mating fashion. Roller 72 is mounted on shaft 82 to be generally movable along axis of the shaft 82. Biasing elements 86 operatively engage both sides of roller 72 and exert a biasing force thereon in both directions along the axis of shaft 82.

In the embodiment shown, biasing elements 86 are comprised of helical springs that are disposed on opposite sides of roller 72 on shaft 82. Washers 88 are provided at the opposite ends of biasing element 86, i.e., the helical springs. A conventional fastener 89 at free end of shaft 82 confines roller 72 between biasing element 86 (helical springs).

Figure 4:
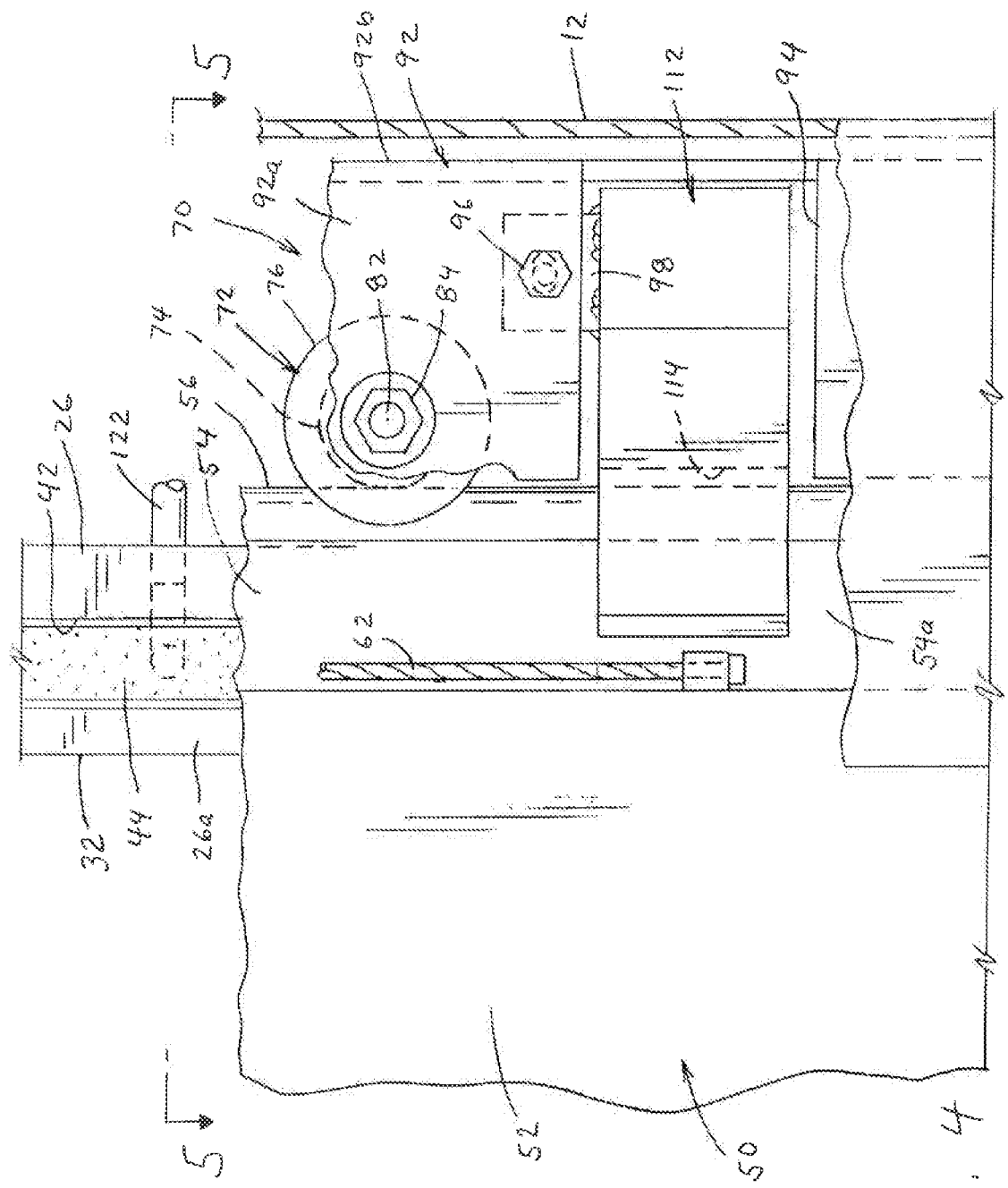
FIG. 4 is an enlarged, partially-sectioned and partially-broken, elevational view of a roller assembly and a clamp assembly that operatively engages the door assembly of the steam sterilizer.

A plurality of spaced-apart door blocks 112 are provided along each side of door assembly 50 in the recesses or notches 94 formed in mounting bracket 92, as best seen in FIGS. 2 and 3. Door blocks 112 are mounted along the sides of access opening 32 to sterilizer chamber 20. In the embodiment shown, bracket 92 is mounted to door blocks 112 by fasteners 96 connected to clips 98 that are welded to door blocks 112, as best seen in FIG. 4.

As best seen in FIGS. 5-7, door blocks 112 are generally C-shaped and define a recess 114. Door block 112 are spaced apart and mounted to side wall 22 of sterilizer chamber 20 such that recess 114 defined in C-shaped door blocks 112 are in registry with the front end face of the front end plate 26 and received edges 56 of door assembly 50, as shown in the drawings. In the embodiment shown, door blocks 112 are generally solid blocks of metal that are welded to side wall 22 of sterilization chamber 20. Recesses 114 in door blocks 112 are dimensioned to receive the outer surface of flanges 54 on door assembly 50. Each door block 112 includes a planar surface 116 that faces in the direction of access opening 32 to sterilizer chamber 20. Door blocks 112 are mounted such that the inward facing surfaces 116 of the door blocks 112 are coplanar to each other and are spaced from an outer planar surface 26a of end plate 26 of the sterilizer chamber 20.

As best seen in FIGS. 5-7, roller assemblies 70 and door blocks 112 are disposed to operatively engage respectively the outer surfaces of flanges 54 of door assembly 50 and to allow flanges 54 of door assembly 50 to move freely within recesses 114 defined by door blocks 112. As illustrated in FIGS. 5-7, edges 56 of door assembly 50 are disposed within the recesses 114 defined by door blocks 112 and are free to move between surface 26a of front end wall 26 and inner facing surfaces 116 of door blocks 112.

Referring now to FIGS. 5, 6 and 7, the operation of door assembly 50 and roller assemblies 70 shall be described. Door assembly 50 is in its first, lowered position during loading and unloading of sterilization chamber 20. Door assembly 50 moves to its second, elevated and closed position during operation of sterilizer 10. Movement of door assembly 50 between the first and second position is guided by roller assemblies 70 mounted to mounting brackets 92. When door assembly 50 is initially in its closed position prior to sealing door assembly 50 and sterilization chamber 20, door assembly 50 and roller assemblies 70 are in a position as shown in FIG. 5. In this position, flanges 54 of door assembly 50 are generally centrally located within recess 114 defined by the door block 112. In this position, inner surface 52a of door assembly 50 is spaced from outward facing surface 26a of front end wall 26 of sterilizer chamber 20. Likewise, the outward facing surface of flanges 54 of door assembly 50 is spaced from the inward facing planar surface 116 of door block 112. As illustrated in FIG. 5, seal element 44 is recessed, i.e., bottomed out, in slot 42 that extends around access opening 32.

An inlet port 122 communicates with the backside of seal element 44. Inlet port 122 allows pressurized gas or steam from a source within sterilizer 10 to force seal element 44 against inner surface 52a of door assembly 50. (A more detailed explanation of the door seal arrangement can be found in the aforementioned U.S. Pat. No. 8,206,660). Introduction of pressure behind seal element 44 forces seal element 44 against inner surface 52a of door assembly 50, thereby forming a seal between door assembly 50 and sterilization chamber 20 from the surrounding environment. With sterilization chamber 20 sealed, a sterilization cycle may be run. Typically, steam would be introduced into the sterilization chamber via a steam inlet line 124, illustrated in FIGS. 5, 6 and 7. During a sterilization cycle, pressure within sterilization chamber 20 may exceed pressure outside of sterilization chamber 20, or a vacuum condition may be established within sterilization chamber 20 during a sterilization cycle wherein the pressure within sterilization chamber 20 is less than the pressure outside of the sterilization chamber 20.

When pressure within sterilization chamber 20 exceeds the surrounding pressure, pressure exerted along inner surface 52a of the door assembly 50 and forces door assembly 50 away from the end face of sterilization chamber 20. This pressure forces door assembly 50 outward away from sterilization chamber 20. An outward facing surface 54a of flanges 54 of door assembly 50 abuts inward facing surface 116 of door block 112 and limits movement of door assembly 50 away from sterilization chamber 20. The back pressure behind seal element 44 causes seal element 44 to maintain sealing engagement with inner surface 52a of door assembly 50.

As illustrated in FIG. 6, because edge 56 of flange 54 of door assembly 50 is captured in recess 78 of roller 72 of roller assembly 70, door assembly 50 causes roller 72 to move outward, i.e., slide along shaft 82 in the direction indicated by the arrow in FIG. 6. In other words, roller 72 moves with door assembly 50 as door assembly 50 is forced away from sterilization chamber 20 by the pressure therein. Door assembly 50 moves in the downward direction in FIG. 6 against the biasing force of the biasing element 86 on the one side of roller 72, as roller 72 moves with flange 54 of door assembly 50.

When a vacuum condition exists within sterilization chamber 20 during a sterilization cycle, the vacuum exerts an inward force on inner surface 52a of door assembly 50 causing door assembly 50 to move toward front end wall 26 and causing inner surface 52a of door assembly 50 to abut the surface 26a of front end wall 26, as illustrated in FIG. 6. In this respect, seal element 44 is forced toward the bottom of annular slot 42, but maintains sealing engagement with inner surface 52a of door assembly 50. As illustrated in FIG. 7, movement of door assembly 50 to this position causes roller 72 to move in the direction of the arrow in FIG. 7 along shaft 82 of roller assembly 70 against biasing element 86, as illustrated.

The foregoing description is a specific embodiment of the present invention. It should be appreciated that this embodiment is described only for the purposes of illustration only, and that numerous alterations and modifications may be practiced by those skilled in the art without departing from the spirit and scope of the invention.

For example, the present invention has been described with roller 72 having an outer surface profile in the form of an annular recess 78 formed about the periphery of roller 72 to receive edge 56 of door assembly 50. In an alternate embodiment, the outer surface profile of edge 56 of door assembly 50 may be in the form of an elongated slot dimensioned to receive the edge of roller 72, wherein roller 72 rolls along in the slot.

Still further, the upper leading end of edge 56 is preferably tapered to facilitate entry into recess 78 of roller 72 as door assembly 50 moves from an opened position to a closed position.

It is intended that all such modifications and alterations be included insofar as they come within the scope of the invention as claimed or the equivalents thereof.

The present invention thus provides a door alignment system that allows limited movement of door assembly 50 in a direction perpendicular to the normal path of moving door assembly 50. The present invention thus eliminates more complex roller and bearing guides that do not easily allow movement transverse to the opening and closing direction of the door. The present invention provides a roller guide system that is easier and simpler than roller tract guide assembly known heretofore.

What is claimed:

1. A door alignment assembly for aligning a door that is movable relative to an opening, the door alignment assembly comprised of:
 a plurality of spaced-apart roller assemblies configured to be aligned along edges of a door to align the door relative to the opening as the door moves between an open and a closed position, each of the roller assemblies comprised of:
 a shaft, a cylindrical roller mounted on the shaft and having an outer annular surface profile extending along a periphery thereof, a first biasing element disposed on a first side of the roller and a second biasing element disposed on a second side of the roller opposite the first side, wherein the roller is movable against the first and second biasing elements axially along the axis of the shaft, wherein the plurality of roller assemblies align the door and allow the door to move along a path in a plane and further allow limited movement of the door in a direction perpendicular to the plane.

2. The door alignment assembly according to claim 1, wherein the first and second biasing elements comprises helical springs.

3. The door alignment assembly according to claim 2, wherein the springs are disposed on the shaft.

4. The door alignment assembly according to claim 1, further comprising the door, wherein the surface profile comprises a recess, and wherein one edge of the door is tapered to facilitate entry of the edge into the recess of the roller assemblies.

5. The door alignment assembly according to claim 4, wherein the surface profile is semi-circular in shape.

6. A The door alignment assembly according to claim 1, wherein the roller is movable on the shaft relative thereto.

7. A door alignment assembly according to claim 4, wherein the door is movable relative to the rollers.

8. The door alignment assembly according to claim 1, further comprising the door, wherein the annular surface profile of the roller engages a mating surface profile on a lateral edge of the door.

9. The door alignment assembly according to claim 1, wherein the first biasing element applies a biasing force to the roller in a first direction along an axis of the shaft, and the second biasing element applies a biasing force to the roller in a second direction along the axis of the shaft, the second direction being opposite the first direction.

10. The door alignment assembly according to claim 9, wherein the first direction and the second direction are parallel to an axis of the shaft.

\* \* \* \* \*